United States Patent
McLeay

(10) Patent No.: US 10,543,273 B2
(45) Date of Patent: *Jan. 28, 2020

(54) ANTI-FIBROBLASTIC FLUOROCHEMICAL EMULSION THERAPIES

(71) Applicant: Matthew T. McLeay, Omaha, NE (US)

(72) Inventor: Matthew T. McLeay, Omaha, NE (US)

( * ) Notice: Subject to any disclaimer, the term of this patent is extended or adjusted under 35 U.S.C. 154(b) by 15 days.

This patent is subject to a terminal disclaimer.

(21) Appl. No.: 15/144,418

(22) Filed: May 2, 2016

(65) Prior Publication Data

US 2016/0317660 A1 Nov. 3, 2016

Related U.S. Application Data

(63) Continuation of application No. 13/175,305, filed on Jul. 1, 2011, now Pat. No. 9,351,943.

(60) Provisional application No. 61/398,824, filed on Jul. 1, 2010.

(51) Int. Cl.

| | |
|---|---|
| *A61K 47/06* | (2006.01) |
| *A61K 9/00* | (2006.01) |
| *A61K 9/12* | (2006.01) |
| *A61K 31/00* | (2006.01) |
| *A61K 9/107* | (2006.01) |
| *A61K 33/00* | (2006.01) |
| *A61K 45/06* | (2006.01) |
| *A61K 47/46* | (2006.01) |

(52) U.S. Cl.
CPC ............ *A61K 47/06* (2013.01); *A61K 9/0048* (2013.01); *A61K 9/0078* (2013.01); *A61K 9/107* (2013.01); *A61K 9/12* (2013.01); *A61K 9/124* (2013.01); *A61K 31/00* (2013.01); *A61K 33/00* (2013.01); *A61K 45/06* (2013.01); *A61K 47/46* (2013.01)

(58) Field of Classification Search
CPC .................................. A61K 9/107; A61K 9/12
See application file for complete search history.

(56) References Cited

U.S. PATENT DOCUMENTS 5,149,319 A * 9/1992 Unger .................... A61K 9/127
424/450
2010/0324276 A1* 12/2010 Sundaram ............ A61K 31/727
536/21

FOREIGN PATENT DOCUMENTS

WO WO98/05301 * 2/1998

OTHER PUBLICATIONS

Stroncek and Puri, Journal of Translational Medicine, 2010, vol. 8, No. 31, pp. 1-2).*
Gioni et al (Molecular Cancer Research, 2008, vol. 5, pp. 706-714).*
Centis et al (Artificial Organs, 2007, vol. 31, pp. 649-653).*
Modi (Breast Cancer Research and Treatment, 2005, vol. 90, pp. 157-163).*
Chappelow and Kaiser (Drugs, 2008, vol. 68, pp. 1029-1036).*
Wynn (Journal of Clinical Investigation, 2007, vol. 117, pp. 524-529).*

* cited by examiner

*Primary Examiner* — Karen A. Canella
(74) *Attorney, Agent, or Firm* — Kutak Rock LLP

(57) ABSTRACT

The present invention is directed to compositions and methods targeting tissue resident cells, such as fibroblasts, in a subject harboring conditions or at risk for conditions that would benefit from anti-fibroblastic therapy. The present invention relates to the use of fluorochemical compositions and methods of delivery that result in retention of the fluorochemical composition and any bioactive agent delivered in combination with the fluorochemical composition.

16 Claims, 11 Drawing Sheets

26 Nov 0900

26 Nov 1800

3 DEC

ANTI-FIBROBLASTIC FLUOROCHEMICAL EMULSION THERAPIES

CROSS-REFERENCE TO RELATED APPLICATION

This application claims benefit of U.S. Provisional Application No. 61/398,824, filed Jul. 1, 2010, which is incorporated herein by reference in its entirety.

FIELD OF THE INVENTION

The present invention generally relates to compositions and methods for the administration of bioactive agents to a subject in need thereof. In particular, the present invention relates to methods, systems, and compositions comprising aerosol fluorochemical emulsions that are directly administered to a target area in a subject and are retained in the target area for a sufficient time to provide a benefit.

BACKGROUND OF THE INVENTION

Fibroblast cell types have been shown to contribute to disease persistence and perpetual damage following injury. Fibroblasts are ubiquitous cells identified by their morphology, production of extracellular matrix and lack of epithelial, vascular and leukocyte lineage markers. They are one of the most abundant cells of the stoma and considered tissue resident cells. While fibroblasts primarily synthesize and remodel the extracellular matrix of tissues, they also have the ability to produce and respond to growth factors allowing paracrine interactions that regulate the morphogenesis of epithelial and endothelial structures in tissues. Thus, fibroblasts play a critical role during tissue development, differentiation and repair in many organs. Presumably, these critical roles for fibroblasts are generally beneficial to a subject, however, deregulation of the molecular mechanisms controlling these critical roles has been found to promote harmful or detrimental affects such as promoting tumor growth, cancer metastases, scar tissue formation, and auto-immunity. For instance, fibroblasts isolated from diseased tissues were shown to be phenotypically different from those taken from normal tissue. Further, fibroblasts have been shown to have a role in cancer at all stages including progression, growth and metastasis. Specifically, at the site of a tumor, the surrounding fibroblasts remain continuously activated, facilitating angiogenesis and cancer progression. In this respect, fibroblasts have great potential as therapeutic targets.

The efficacy of many pharmaceutical agents is predicated on their ability to proceed to the selected target sites and remain there in effective concentrations for sufficient periods of time to accomplish the desired therapeutic or diagnostic purpose. Difficulty in achieving efficacy may be exacerbated by the location and environment of the target site as well as by the inherent physical characteristics of the compound administered. For example, drug delivery via routes subject to repeated drainage or flushing as part of the body's natural physiological functions offer significant impediments to the effective administration of pharmaceutical agents. In this respect, delivery and retention problems are often encountered when administering compounds through the respiratory or gastrointestinal tracts. Repeated administration of fairly large doses is often required to compensate for the amount of drug washed away and to maintain an effective dosing regimen when employing such routes. Such reductions in delivery and retention time complicate dosing regimes, waste pharmaceutical resources and generally reduce the overall efficacy of the administered drug.

In the art, fluorocarbon liquids have been used for treatment of respiratory distress syndrome by removal of lung debris, inflammatory cells and materials by lavage, and by facilitating oxygen delivery. In this capacity, fluorocarbons are used as neat formulations (i.e. liquid formulation with no emulsifying agents). While partial liquid ventilation using perfluorocarbons was shown to improve oxygenation and decrease lung injury in various animal models, clinical trials concluded that neither a high dose nor low dose of perfluorocarbon improved outcome in patients with respiratory distress (See, Kacmarek R M, et al. AM J Respir Crit Care Med. 2006 Apr. 15; 173(8):882-9). Essentially, the perfluorocarbon administered to the patients evaporated before being effective. Larger amounts did not compensate for the evaporation and were not well tolerated by patients.

Accordingly, a need exists for therapeutics and therapeutic delivery vehicles with improved efficacy and target site retention while at the same time minimizing dosage. Also needed is a therapeutic capable of targeting tissue-resident cells and exhibiting anti-fibroblastic activity. The compositions and methods of the present invention provide such anti-fibroblastic therapeutics and therapeutic delivery vehicles with improved efficacy and target site retention while minimizing dosage of toxic agents.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

SUMMARY OF THE INVENTION

Figure 1:
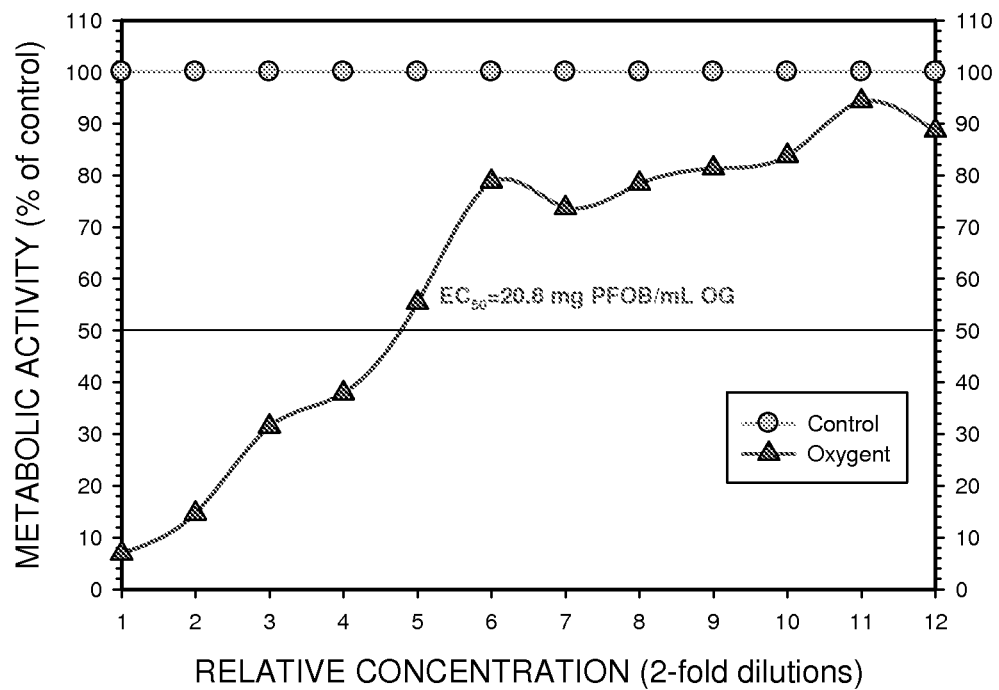
FIG. 1 graphically illustrates the effect of aerosol perfluorocarbon emulsion composition on the growth of breast cancer fibroblast cells.

The present invention is directed to compositions and methods targeting tissue resident cells, such as fibroblasts, in a subject harboring conditions or at risk for conditions that would benefit from anti-fibroblastic therapy. The present invention relates to the use of aerosolized fluorochemical compositions and methods of delivery that result in retention of the fluorochemical composition and any bioactive agent delivered in combination with the fluorochemical composition to the targeted site.

Methods of the present invention include directly administering an aerosol fluorochemical composition of the invention to a subject. In a preferred embodiment, the fluorochemical composition is an emulsion. In another embodiment the fluorochemical composition is instilled to the target site. The fluorochemical composition may be administered with a bioactive agent. Further, the fluorochemical composition may be administered with oxygen. The oxygen may be delivered by oxygenating the fluorochemical composition or directly to the subject.

Methods of the invention include using an aerosolized fluorochemical composition as a therapeutic delivery vehicle for bioactive agents. The fluorochemical composition may include at least one bioactive agent. The fluorochemical composition can also be used in conjunction with a bioactive agent as a pre-treatment. The pre-treatment with a fluorochemical composition will aide in enhanced oxygenation causing increased retention and treatment of the bioactive agent on the target.

Methods of the invention include using a fluorochemical composition alone as a therapeutic agent that synergistically enhances benefits of additional therapies. For instance, a fluorochemical composition may be used to sensitize an area to irradiation or chemotherapy treatment.

Methods of the invention include using fluorochemical compositions in imaging applications such as diagnostic imaging.

The methods of the invention are useful in treating fibroblastic conditions. In particular, the methods of the invention are used to treat subjects with cancer, tissue injury, pulmonary distress, spinal cord injury, or macular degeneration.

DETAILED DESCRIPTION

In accordance with the present invention, a composition that is capable of targeting tissue resident cells and modulating their activity as well as methods of use have been discovered. The invention finds use in targeting tissue resident cells, such as fibroblasts, in a subject harboring conditions or at risk for conditions that would benefit from anti-fibroblastic therapy. In particular, the invention relates to the use of aerosolized fluorochemical compositions for use as a delivery mechanism to targeted tissue that results in retention of the aerosolized fluorochemical composition and any bioactive agent delivered in combination with the fluorochemical composition. Further, the invention relates to a therapeutic treatment method that includes a combination of the fluorochemical composition and bioactive agent to create a therapeutic composition which is aerosolized for delivery retention by, to and treatment of the target.

I. Compositions

Compounds useful in this invention, such as those listed below (hereinafter called "fluorocarbons" or "fluorochemicals") are generally able to promote gas exchange, and most of these fluorocarbons readily dissolve oxygen and carbon dioxide.

A. Fluorocarbons

Fluorocarbon molecules used in the present invention may have various structures, including straight or branched chain or cyclic structures as known in the art. These molecules may also have some degree of unsaturation, and may also contain bromine or hydrogen atoms, or they may be amine derivatives. Typically, the fluorocarbon is a liquid or a gas at room temperature (25° C.). Preferably, the fluorocarbon has from about 2, 3, 4, or carbon atoms to about 10, 12, or 14 carbon atoms. There are a number of fluorocarbons that are contemplated for use in the present invention. These fluorocarbons include but are not limited to bis(F-alkyl) ethanes such as $C_4F_9CH=CH_4CF_9$ (sometimes designated "F-44E"), i-$C_3F_9CH=CHC_6F_{13}$ ("F-i36E"), and $C_6F_{13}CH=CHC_6F_{13}$ ("F-66E") cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di- or F-trimethylbicyclo[3,3,1]nonane ("nonane"); perfluorinated amines, such as F-tripropylamine ("FTPA") and F-tri-butylamine ("FTBA"), F-4-methyloctahydroquinolizine ("FMOQ"), F-n-methyl-decahydroisoquinoline ("FMIQ"), F-n-methyl-decahydroquinoline ("FHQ"), F-n-cyclohexylpurrolidine ("FCHP"), F-2-butyltetrahydrofuran ("FC-75" or "RM101") and other fluorocarbons known in the art.

Other fluorocarbons include brominated perfluorocarbons, such as but not limited to 1-bromo-heptadecafluorooctane ($C_8F_{17}Br$, sometimes designated perfluorooctylbromide or "PFOB"), 1-bromopenta-decafluoroheptane ($C_7F_{15}Br$), and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long. Also contemplated are fluorocarbons having nonfluorine substituents, such as perfluorooctyl chloride, perfluorooctyl hydride, and similar compounds having different numbers of carbon atoms.

Additional fluorocarbons contemplated in accordance with this invention include perfluoroalkylated ethers or polyethers, such as but not limited to $(CF_3)_2CFO(CF_2CF_2)_2OCF(CF_3)_2$, $(CF_3)_2CFO-(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example compounds having the general formula $C_nF_{2n+1}-C_{n'}F_{2n'+1}$, $C_nF_{2n+1}OC_{n'}F_{2n'+1}$, or $C_nF_{2n+1}CF=CHC_{n'}F_{2n'+1}$, where n and n' are the same or different and are from about 1 to about 10 (so long as the compound is a liquid at room temperature). Such compounds, for example, include but are not limited $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed herein, but having those properties described in this disclosure that would lend themselves to use in accordance with the present invention are additionally contemplated.

The flurorcarbons used in the present invention may be used as neat liquid compositions, as gases, or as emulsions.

B. Fluorocarbon Emulsions

In one embodiment, the fluorocarbon compositions of the present invention will include an emulsifying agent to create a fluorocarbon emulsion. Such emulsions are typically fluorocarbon-in-water emulsions having a discontinuous fluorocarbon phase and a continuous aqueous phase. In an additional embodiment, emulsions with a continuous fluorocarbon phase and a discontinuous aqueous phase are also contemplated. The emulsions typically include any emulsifying agents used or known in the industry including but not limited to, osmotic agents, buffers, electrolytes and combinations thereof.

Although concentrations from about 1% to 5% are possible and contemplated as low as 5% w/v are also possible. In another embodiment the concentrations are about 5% to at least 25% or 30%, preferably at least 40%, 50%, 55%, and may be 60%, 75% or 80% w/v. In an additional embodiment emulsions of up to 85%, 90%, 100%, and 125% are also contemplated. Preferred fluorocarbon emulsion formulations are known in the art and include without limitation those disclosed in U.S. Pat. Nos. 4,865,836; 4,987,154; 4,927,623; and 6,204,296 which are hereby incorporated by reference.

1. The Emulsifying Agent

The fluorocarbon emulsions can also include an emulsifying agent. As used in this specification, an emulsifying agent is any compound or composition that aids in the formation and maintenance of the droplets of the discontinuous phase by forming a layer at the interface between the discontinuous and continuous phases. The emulsifying agent may comprise a single compound or any combination of compounds, such as in the case of co-surfactants.

In the present invention, emulsifying agents can include compounds known in the industry but are not limited to phospholipids, nonionic surfactants, fluorinated surfactants, which can be neutral or anionic, and combinations of such emulsifying agents.

Lecithin is a phospholipid that has frequently been used as a fluorocarbon emulsifying agent, as is more fully described in U.S. Pat. No. 4,865,836. Another example of an emulsifying agent for use with fluorochemical compositions is egg yolk phospholipids. See e.g., Long, U.S. Pat. No. 4,987,154.

Other emulsifying agents may be used with good effect, such as fluorinated surfactants, also known as fluorosurfactants. Fluorosurfactants that can provide stable emulsions include triperfluoroalkylcholate; perfluoroalkylcholestanol; perfluoroalkyloxymethylcholate; $C_3F_7O(CF_2)_3C(=O)NH(CH_2)_3N(O)(CH_3)_2$(XMO-10); and fluorinated polyhydroxylated surfactants, such as, for example, those discussed in "Design, Synthesis and Evaluation of Fluorocarbons and Surfactants for In Vivo Applications New Perfluoroalkylated Polyhydroxylated Surfactants" by J. G. Riess, et al. J. G. Riess et al.; Biomat. Artif. Cells Artif. Organs 16: 421-430 (1988).

The nonionic surfactants suitable for use in the present invention include polyoxyethylene-polyoxypropylene copolymers. An example of such class of compounds is Pluronic, such as Pluronic F-68. Anionic surfactants, particularly fatty acids (or their salts) having 12 to 24 carbon atoms, may also be used. One example of a suitable anionic surfactant is oleic acid, or its salt, sodium oleate.

It will be appreciated that choice of a particular emulsifying agent is not central to the present invention. A number of emulsifying agents can be used and will depend on the target, fluorochemical, and bioactive agents used. Indeed, virtually any emulsifying agent (including those still to be developed) capable of facilitating formation of a fluorocarbon-in-water emulsion can form improved emulsions when used in the present invention. The optimum emulsifying agent or combination of emulsifying agents for a given application may be determined through empirical studies that do not require undue experimentation. Consequently, one practicing the art of the present invention should choose the emulsifying agent or combination of emulsifying agents for such properties as biocompatibility.

2. Preparation of the Emulsion

Fluorocarbon emulsions according to the invention are prepared by means of conventional emulsification procedures, such as, for example, mechanical or ultrasonic emulsification of an emulsion formulation in a Manton-Gaulin mixer or Microfluidizer (Microfluidics Corp., Newton, Mass.). Any means known in the industry for creating an emulsion can be used.

Usually, a pre-emulsion mixture is prepared by simple mixing or blending of the various components. This pre-emulsion is then emulsified in the desired emulsification apparatus.

The combined fluorocarbon concentration in the emulsion is preferably anywhere within the range of about 20% to about 125% (w/v). In another embodiment the fluorocarbon concentration is 5% to about 20%. In preferred emulsions, the total perfluorocarbon concentration is from about 30%, 40%, or 50% to about 70%, 80%, 90%, or 100% (w/v). Emulsifiers are added in concentrations of from about 0.1% to 10%, more preferably 1% or 2% to about 6% (w/v).

C. Bioactive Agents

In one embodiment the fluorocarbon composition is combined with a bioactive compound to create a therapeutic agent. In another embodiment the fluorocarbon composition alone is the therapeutic agent. In certain embodiments, more than one bioactive or therapeutic agent may be combined with the fluorocarbon and administered to a subject. Such compounds may be administered to the subject simultaneously or sequentially. A fluorochemical composition of the invention may be administered to a subject in conjunction with at least a second compound known in the art to benefit the target microenvironment. For example, a fluorochemical composition may be administered to a subject in conjunction with a bioactive agent. The amount of bioactive agent will depend on desired dosage prescribed to treat the target.

Suitable bioactive agents include any therapeutic, bioactive, or diagnostic compound or composition known in the art or yet to be discovered, as well as combinations thereof, that may be administered to a subject. The precise amount of bioactive agent used in combination with the composition of the present invention is dependent upon the target, the agent of choice, the required dose, and the form of the agent actually combined with the composition. Those skilled in the art will appreciate that such determinations may be made by using well known techniques in combination with the teachings of the present invention.

Preferred bioactive agents may comprise but are not limited to respiratory agents, antibodies, antibiotics, antivirals, mydriatics, antiglaucomas, anti-inflammatories, antihistaminetics, antineoplastics, anethetics, ophthalmic agents, cardiovascular agents, active principles, nucleic acids, genetic material, immunoactive agents, imaging agents, immunosuppressive agents, astrointestinal agents and combinations thereof. Further exemplary embodiments of the present invention comprise anti-inflammatory agents such as the glucocorticosteroids (i.e. cortisone, prednisone, prednisolone, dexamethasone, betamethasone, Beclomethasone diproprionate, Triamcinolone actinide, Flunisolide) xanthines (i.e. theophylline, caffeine), antibiotics (i.e. aminoglycosides, penicillins, cephalosporins, macolides, quinolones, tetracyclines, chloramphenicol), bronchodilators such as the $B_2$-agonists (i.e. adrenaline, isoprenaline, salmeterol, albuterol, salbutamol, terbutaline, formoterol) and surfactgants. Still other exemplary embodiments include a/B adrenergic blockers (i.e. Normodyne®, Trandate®), angiotensin converting enzyme inhibitors (i.e. Vasotec®), antiarrhythmics, beta blockers, calcium channel blockers, inotropic agents, vasodilators, vasopressors, anesthetics (i.e. morphine) and ophthalmic agents (i.e. Polymyxin B, Neomycin, Gramicidin).

Other exemplary embodiments include anti-cancer agents such as chemotherapy agents including, without limitation, actinomycin D (Cosmegen), aldesleukin (Proleukin), alitretinoin (Panretin), all-trans retinoic acid/ATRA (Tretinoin), altretamine (Hexalen), amascrine, asparaginase (Elspar), azacitidine (Vidaza), azathioprine (Imuran), bacillus calmette-guerin/BCG (TheraCys, TICE BCG, TICE), bendamustine hydrochloride (Treanda), bexarotene (Targretin), bicalutamide (Casodex), bleomycin (Blenoxane), bortezomib (Velcade), busulfan (Busulfex, Myleran), capacitabine (Xeloda), carboplatin (Paraplatin), carmustine bcnu (BiCNU), chlorambucil (Leukeran), cisplatin/cisplatinum (Platinol, Platinol-AQ), cladribine (Leustatin), cyclophosphamide/cytophosphane (Cytoxan, Endoxan, Neosar, Procytox, Revimmune), cytabarine (Cytosar-U), dacarbazine (DTIC-Dome), daunorubicin/daunomycin (DaunoXome, Cerubidine), denileukin diftitox (Ontak), dexrazoxane (Zinecard), docetaxel (Taxotere), doxorubicin (Adriamycin, Rubex), doxorubicin (Doxil), doxorubicin liposomal (Doxil), epirubicin (Ellence), etoposide (Eposin, Etopophos, Toposar, Vepesid, VP-16), fludarabine (Fludara), fluorouracil 5-FU (Adrucil), gemcitabine (Gemzar), goserelin (Zolodex), hydrocortisone (Solu-Cortef), hydroxyurea (Hydrea), idarubicin (Idamycin), ifosfamide (Hex, Mitoxana), interferon alfa (Intron-A, Roferon-A), irinotecan CPT-11 (Camptosar), lapatinib (Tykerb), lenalidomide (Revlimid), leuprolide (Eligard, Lupron, Lupron Depot, Viadur), mecholorethamine/chlormethine/mustine/HN2 (Mustargen), mercaptopurine (Purinethol), methotrexate (Rheumatrex), methylprednisolone (Solu-Medrol), mitomycin (Mutamycin), mitotane (Lysodren), mitoxantrone (Novantrone), octreotide (Sandostatin, Sandostatin LAR), oprelvekin (Neumega), oxaliplatin (Eloxatin, Oxaliplatin Medac), paclitaxel (Taxol, Onxal), paclitaxel protein-bound (Abraxane), pamidronate (Aredia), pazopanib (Votrient), pegaspargase (Oncospar), pegfilgrastim (Neulasta), PEG interferon (PEG-INTRON), Pemetrexed (Alimta), Pentostatin (Nipent), Phenylalanine mustard (Alkeran), plicamycin/mithramycin (Mithracin), prednisone (Deltasone, Liquid Pred, Meticorten, Orasone), prednisolone (Delta-Cortef, Orapred, Pediapred, Prelone), procarbazine (Matulane), raloxifene (Evista), romiplostim (Nplate), sargramostim (Leukine), sorafenib (Nexavar), streptozocin (Zanosar), sunitinib (Sutent), tamoxifen (Novaldex), temozolomide (Temodar), temsirolimus (Torisel), teniposide (Vumon, VM-26), thalidomide (Thalomid), thioguanine (Thioguanine Tabloid), thiophosphoamide/thiotepa (Thioplex), thiotepa (Thioplex), topotecan hydrochloride (Hycamtin), toremifene (Fareston), tretinoin (Vesanoid), valrubicin (Valstar), vinblastine (Velban, Alkaban-AQ), vincristine (Oncovin, Vincasar, Vincrex), vindesine (Eldisine), vinorelbine (Navelbine), vorinostat (Zolinza), and zoledronic acid (Zometa).

Anti-cancer agents also include antibody based therapies including, without limitation, alemtuzumab (Campath), bevacizumab (Avastin), cetuximab (Erbitux), gemtuzumab ozogamicin (Mylotarg), ibritumomab tiuxetan (Zevalin), ofatumumab (Arzerra), panitumumab (Vectibix), rituximab (Rituxan, Mabthera), tositumomab (Bexxar), trastuzumab (Herceptin), and trastuzumab DM1 (Herceptin DM1).

Further, anti-cancer agents include tyrosine-kinase inhibitor based therapies including, without limitation, axitinib, bafetinib, bosutinib, cediranib (Recentin), crizotinib, dasatinib (Sprycel), erlotinib hydrochloride (Tarceva), gefitinib (Iressa), imatinib (Gleevec, Glivec), lapatinib (Tykerb/Tyverb), lestaurtinib, neratinib, nilotinib (Tasigna), ponatinib, quizartinib, regorafenib, ruxolitinib, sunitibin (Sutent), tofacitinib, vandetanib (Zactima), N-acetylcysteine, and vatalanib. In addition the anti-cancer agent can include anti-virals including by not limited to Ribavirin.

In accordance with the present invention, those skilled in the art will appreciate that various bioactive agents may be used in combination with the compositions of the present invention and selection of the bioactive agents used depends upon the intended use of the invention. Further, those skilled in the art will appreciate that various forms of these compounds may be used to modify the therapeutic index of the bioactive agents.

Because the compositions of the present invention are uniquely suited for use in a wide variety of physiological applications such as ocular, oral, pulmonary, rectal, subcutaneous, intramuscular, intraperitoneal, nasal, vaginal, or aural administration of medicaments or diagnostic compounds, a wide variety of bioactive agents may be incorporated therein. Accordingly, the foregoing list of bioactive agents is not intended to limit the present invention in any way.

Another advantage provided by the present invention is the ability to use the free base form of the incorporated bioactive agent rather than its less efficacious salt form. That is, the efficacy of lipophilic forms of drugs have been shown in many instances to be more potent than the less lipophilic forms of the agent, (i.e. the salts). The nonreactive nature of the fluorochemical compositions allow the incorporation of particularly efficacious base forms of the selected pharmaceutical agent. As those skilled in the art will appreciate, the use of these more potent agent forms enhances the bioavailability of the incorporated pharmaceutical agent and reduces the dosages which must be administered.

The present invention may optionally contain at least one nonfluorinated co-solvent to facilitate the combination of a bioactive agent in the fuorochemical composition. Preferably, the concentration of the nonfluorinated co-solvent comprises up to about 50% v/v of the fluorochemical composition. Suitable co-solvents include any of those known in the art or yet to be discovered. Exemplary co-solvents include ethers, alcohols, alkyl sulfoxides and combinations thereof. Preferably the co-solvents are short chain alcohols (i.e. carbon chain length ≤4 carbons) or an alkyl sulfoxide such as dimethylsulfoxide. More preferably, the co-solvent is ethanol.

The compositions of the present invention may optionally include one or more additives. Any additive that provides benefit to the intended use of the present invention is contemplated and includes additives known in the art and yet to be discovered. Exemplary additives include mineral salts, buffers, oncotic and osmotic agents, nutritive agents, flavorings or palatability enhancers, or any other ingredient capable of augmenting the favorable characteristics of the compositions of the present invention including pharmaceutical stability, therapeutic efficacy and tolerance.

II. Methods

The present invention encompasses methods of targeting tissue resident cells, such as fibroblasts, in a subject harboring conditions or at risk for conditions that would benefit from anti-fibroblastic therapy. The methods may be utilized to treat a subject harboring a condition that would benefit from anti-fibroblastic therapy or that is at risk of developing a condition that would benefit from anti-fibroblastic therapy.

A. Conditions Benefiting from Anti-fibroblastic Therapy

Fibroblastic conditions that would benefit from anti-fibroblastic therapy such as treatment with the fluorochemical composition may include any condition or disease that is altered from normal physiological homeostasis. For instance, exemplary fibroblastic conditions that may benefit from anti-fibroblastic therapy include but are not limited to sites of tissue injury, degeneration, neoplastic growth, tumor formation, tumor growth, cancer, broncho pulmonary dysplasia, osteoarthritis, and other conditions known in the art or yet to be discovered that may benefit from anti-fibroblastic therapy. Exemplary fibroblastic conditions may include, without limitation, acneiform eruptions, acute interstitial pneumonitis, autoinflammatory syndromes, arthritis, asthma, atherosclerosis, autoimmune diseases, bronchiolitis obliterans with organizing pneumonia, cancer chlorioretinal scarring, chronic blistering, chronic prostatitis, cirrhosis, colitis, connective tissue diseases, corneal scarring, Crohn's disease, dermal and subcutaneous growths, dermatitis, dermatomyositis, desquamative interstitial pneumonitis, diverticulitis, eosinophilic cutaneous conditions, epidermal cysts, epidermal neoplasms, epidermal nevi, fibromyaligia, glaucoma, glomerulonephritis, hepatitis, hypertrophic scarring, inflammatory bowel diseases, inflammatory demyelinating polyneuropathy, inflammatory myopathies, interstitial cystitis, interstitial lung disease, irritable bowel syndrome, ischaemic heart disease, keloidal scarring, Lofgren syndrome, lupus, lupus erythematous, lymphocytic interstitial pneumonitis, macular degeneration, nephritis, nonspecific interstitial pneumonitis, osteoporosis, Parkinson's, pelvic adhesive disease, pelvic inflammatory disease, polymyalgia rheumatica, polymyositis, reperfusion injury, respiratory distress, respiratory bronchiolitis, rheumatoid arthritis, sarcoidosis, skin grafts, spinal cord injuries, surgical scarring, systemic sclerosis, transplant rejection, ulcerative colitis, and vasculitis as well as others known in the art or yet to be discovered.

Also, methods of the invention may be utilized to treat a population of cells that would benefit from anti-fibroblastic therapy. Such cells include those in a subject as well as those removed from a subject for therapeutic treatment, cultured cells, those used in gene-therapy practices, and any other cell that may benefit from anti-fibroblastic therapy. For instance, stem cells may benefit from anti-fibroblastic therapy to remove fibroblasts used during culturing techniques but no longer needed.

B. Methods of the Invention

Generally, methods of the present invention include administering to a subject an aerosolized fluorochemical composition of the invention for use as a delivery mechanism to targeted cells and tissue. In another embodiments, the aerosolized fluorochemical composition is an emulsion used to deliver to and enhance the retention of therapeutic agents at targeted cells and tissues. In another embodiment, the aerosolized fluorochemical composition is itself a therapeutic agent. In another embodiment, the fluorochemcial composition is delivered via installation (instilling) and can include the therapeutic agent.

In certain embodiments, the fluorochemical composition is administered in combination with oxygen. By way of example, the fluorochemical composition may be oxygenated before administration or administered in combination with oxygen. For example, oxygen may be added directly to the composition or provided to the subject through other means such as breathing of oxygen. Suitable sources of oxygen include those known in the art such as carbogen, oxygen, and hyperbaric oxygen.

Methods of the invention include administering to a subject a fluorochemical composition as a therapeutic agent that has anti-fibroblastic activity. Preferably, the fluorochemical composition is administered as an aerosolized emulsion.

Methods of the invention include administering to a subject an aerosolized fluorochemical composition as a delivery vehicle for other agents including agents used in imaging applications or bioactive agents. The properties and characteristics of an aerosolized fluorochemical composition specifically target the composition and enhance the retention of the composition at target sites. Also, the properties and characteristics of a fluorochemical emulsion composition specifically aide in delivery of the composition (including the agent) to the target and enhance the retention of the composition at target sites (see FIGS. 7a and 7b). Use of an aerosolized fluorochemical emulsion synergistically enhances targeting and retention of the agent at target sites. Further, the activity of the fluorochemical acts with the agent causing a synergistic therapeutic effect. In one embodiment, the fluorochemical composition includes an emulsifying agent to create a fluorochemical emulsion composition that is aerosolized for delivery and treatment of the target. In another embodiment the fluorochemical composition is in a neat form without an emulsifying agent. In yet another embodiment, the fluorochemical composition is instilled to the target location. The fluorochemical composition may be used to target an agent to a location in a subject such that the retention time of the agent is improved compared to using the agent alone. The agent may be combined with the fluorochemical composition prior to administration. The fluorochemical composition and agent may work synergistically to benefit the subject. Preferably, the combination is administered as an aerosol. Preferably, the fluorochemical composition include an emulsifying agent to create a fluorochemical emulsion.

Another embodiment includes administering to a subject a fluorochemical composition of the invention prior to a secondary therapy, and/or sensitizing the target area before the secondary therapy. Suitable secondary therapies include irradiation therapy, chemotherapy, combinations thereof and other therapies known in the art or yet to be discovered that would have enhanced efficacy following sensitization of the target area with compositions of the present invention. In one embodiment, the fluorochemical composition is used as a pre-treatment to the target area. Delivery of the fluorochemical composition as a pre-treatment enhances the oxygenation of the target area creating a better environment for enhancing the efficacy of the treatment therapeutic at the target area.

Methods of the invention also include administering compositions of the present invention to an injury site such as a spinal injury. In one embodiment, the fluorochemical composition is aerosolized. In another embodiment, the fluorochemical composition is instilled. In one embodiment, the fluorochemical composition is directly delivered to the injury site, and not through an intravenous delivery. In one embodiment, the fluorochemical composition is an emulsion. In another embodiment, the fluorochemical composition is in neat liquid form without an emulsifying agent. For instance, the compositions are directly instilled either alone or with other therapeutics in a push pull method. A catheter tip is placed above the injury and the fluorochemical composition is instilled with oxygen and the fluid is collected below the injury and re-oxygenated. This process is continued for 1 to 48 hours and can be repeated if necessary.

Methods of the invention include administering compositions of the present invention to an eye injury including macular degeneration. Preferably, the composition is a fluorochemical emulsion. In one embodiment, the compositions are directly aerosolized either alone or in combination with other agents. In another embodiment, the compositions are directly instilled either alone or in combination with other agents.

Methods of the invention include administering compositions of the present invention to a subject for the treatment of cancer. In one embodiment, the fluorochemical composition is aerosolized. In another embodiment, the fluorochemical composition is instilled. In one embodiment, the fluorochemical composition includes an emulsifying agent. In another embodiment, the fluorochemical composition is in a neat form without an emulsifying agent. For instance, the compositions are directly instilled or aerosolized at the site of tumor growth either alone or in combination with other therapeutics and oxygen. Such methods are beneficial in the treatment of any and all cancer types known in the art or yet to be discovered. Exemplary cancer types to be treated include but are not limited to acute lymphoblastic leukemia, acute myeloid leukemia, adrenocortical carcinoma, anaplastic large cell lymphoma, appendix cancer, basal cell carcinoma, B cell cancer, bile duct cancer, bladder cancer, bone cancer (IGF-1 sensitive bone tumors), brain cancer, breast cancer, carcinoid tumor, cardiovascular cancer, cervical cancer, chronic lymphocytic leukemia, chronic myelogenous leukemia, colon cancer, colorectal cancer, epithelial carcinoma, epithelial cell-derived neoplasia, esophageal cancer, Ewing's sarcoma, gastric carcinoma, gastrointestinal cancer, gastrointestinal stromal tumors, glioblastoma multiforme, head and neck cancer, Hodgin's lymphoma, kidney cancer, leukemia, lip cancer, liver cancer, lymphocytic leukemia, lymphoma, lung cancer, medulloblastoma, merkel cell carcinoma, melanoma, mouth cancer, multiple myeloma, Non-Hodgkin's lymphoma, non-small cell lung cancer, oropharyngeal cancer, osteosarcoma, ovarian cancer, pancreatic cancer, prostate cancer, rectal cancer, renal cell carcinoma, retinoblastoma, skin cancer (squamous cell cancer, basal cell cancer), small bowel cancer, small intestine cancer, soft tissue sarcoma, stomach cancer, and testicular cancer as well as other cancers known in the art.

Methods of the invention include using aerosolized fluorochemical compositions in imaging applications. In another embodiment, the fluorochemical composition is instilled for imaging applications. In one embodiment, the fluorochemical composition includes an emulsifying agent. In another embodiment, the fluorochemical composition does not include an emulsifying agent and is used in net form. Suitable imaging applications are known in the art and include without limitation diagnostic imaging such as radiography, magnetic resonance imaging (MRI), scintigraphy (scint), positron emission tomography (PET), and computed tomography (CT) as well as others known in the art. In another embodiment, the fluorochemical composition is used in conjunction or mixed with a monoclonal antibodies to aide in imaging and diagnostics.

C. Delivery Means and Routes

Methods of administration include any method known in the art or yet to be discovered. Exemplary administration methods include intravenous, intraocular, intratracheal, oral, rectal, topical, intramuscular, intraarterial, intrahepatic, intrathoracic, intrathecal, intracranial, intraperitoneal, intrapancreatic, intrapulmonary, or subcutaneously.

The fluorochemical composition may be administered directly by instillation or as an aerosol. One skilled in the art will appreciate that the route of administration and method of administration depend upon the intended use of the compositions, the location of the target area, and the condition being treated in addition to other factors known in the art such as subject health, age, and physiological status. A skilled artisan will also recognize that methods using aerosol compositions may use a catheter placed through an appropriate scope and aerosolizing the composition using a nebulizer. Suitable nebulizers are known in the art. Exemplary nebulizers include but are not limited to the Aeroprobe™, Microsprayer™, Aerotech II™, Pari™ brand, or Aeroclipse™. Alternatively, the compositions may be aerosolized using dry methods known in the art such as a dry powder inhaler or similar device.

Fluorochemical compositions of the invention are typically administered to a subject in an amount sufficient to provide a benefit to the target microenvironment of the subject. This amount is defined as a "therapeutically effective amount." The therapeutically effective amount will be determined by the efficacy or potency of the particular composition, the duration or frequency of administration, and the size and condition of the subject, including that subject's particular treatment response. Additionally, the route of administration should be considered when determining the therapeutically effective amount. It is anticipated that the therapeutically effective amount of a fluorochemical composition of the invention will range from about 0.1 ml/kg to about 35 ml/kg. Depending on the target area and desired therapeutic agent used in conjunction (of in certain instances no additional therapeutic agent will be used) with the fluorochemical composition the amount of fluorochemical can include 0.01%, 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the total therapeutic composition. In determining the therapeutically effective amounts, one skilled in the art will also consider the existence, nature, and extent of any adverse effects that accompany the administration of a particular compound in a particular subject.

III. Kits

The present invention provides articles of manufacture and kits containing materials useful for treating the conditions described herein. The article of manufacture may include a container of a compound as described herein with a label. Suitable containers include, for example, bottles, vials, and test tubes. The containers may be formed from a variety of materials such as glass or plastic. The container holds a composition having an active agent which is effective for treating, for example, conditions that benefit from anti-fibroblastic therapy. The active agent is at least one fluorochemical composition of the invention and may further include additional fluorochemicals or bioactive agents known in the art for treating the specific condition. The label on the container may indicate that the composition is useful for treating specific conditions and may also indicate directions for administration.

Definitions

As used herein, "administering" is used in its broadest sense to mean contacting a subject with a composition of the invention.

The phrase "anti-fibroblastic activity" refers to a characteristic of the fluorochemical compositions of the present invention. The anti-fibroblastic activity includes inhibiting at least one activity ascribed to fibroblast type cells temporarily, transiently, or constitutively. Such activities include without limitation, cell signaling to or from the fibroblast cell, motility, growth, proliferation, differentiation, and other activities of fibroblast cells known in the art or yet to be discovered. The term "fibroblast" refers to cell types known in the art as fibroblast type cells and includes all cell types capable of exhibiting fibroblast like characteristics. Exemplary cells include without limitation, mesenchymal stem cells, fibroblast precursor cells, stromal cells, tissue resident cells and cells yet to be discovered to have fibroblast characteristics.

The phrase "oxygen deprived microenvironment" is used herein to refer to microenvironments that would benefit from the presence of bioavailable oxygen. Exemplary oxygen deprived microenvironments include without limitation areas of tissue injury, tumor growth, metastases, and hypoxic environments. Also included are microenvironments that would benefit from inhibition of fibroblast proliferation and growth. Such microenvironments include a population of cells cultured ex vivo or in vitro.

As used herein, "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific values (e.g., captive or free specimens of endangered species), or mammals which otherwise have value. Suitable subjects also include: mice, rats, dogs, cats, ungulates such as cattle, swine, sheep, horses, and goats, lagomorphs such as rabbits and hares, other rodents, and primates such as monkeys, chimps, and apes. In some embodiments, subjects may be diagnosed with a fibroblastic condition, may be at risk for a fibroblastic condition, or may be experiencing a fibroblastic condition. Subjects may be of any age including new born, adolescence, adult, middle age, or elderly.

The terms "target" and "target site" refer to any site that would benefit from receiving the compositions of the present invention. The terms include cells, tissues, aberrant growths, tumors, cancerous lesions, and other sites that may benefit from the compositions of the invention.

The phrase "therapeutically effective amount" is used herein to mean an amount sufficient to increase to some beneficial degree, preferably to increase by at least about 1 to 100 percent, more preferably by at least about 5 to 95 percent, and more preferably by at least 8 percent or higher, anti-fibroblastic activity as compared to untreated controls. An "effective amount" is a pharmaceutically-effective amount that is intended to qualify the amount of an agent or compound, that when administered to a subject, will achieve the goal of inhibiting an activity of a fibroblast cell or otherwise benefiting the recipient environment.

As various changes could be made in the above compositions and methods without departing from the scope of the invention, it is intended that all matter contained in the above description and in the Examples given below, shall be interpreted as illustrative and not in a limiting sense.

EXAMPLES

The following examples are simply intended to further illustrate and explain the present invention. The invention, therefore, should not be limited to any of the details in these examples.

Example 1

Treatment of Breast Cancer Cells

The ability of aerosolized fluorocarbons to dissolve and carry large amounts of oxygen makes them a novel anti-cancer therapeutic that may reduce tumor hypoxia and the extracellular acidosis moat that protect cancers from effective therapy. To analyze the effectiveness of fluorocarbons as an anti-cancer therapeutic, the growth of cancer cells was measured in the presence and absence of fluorocarbons.

Figure 2:
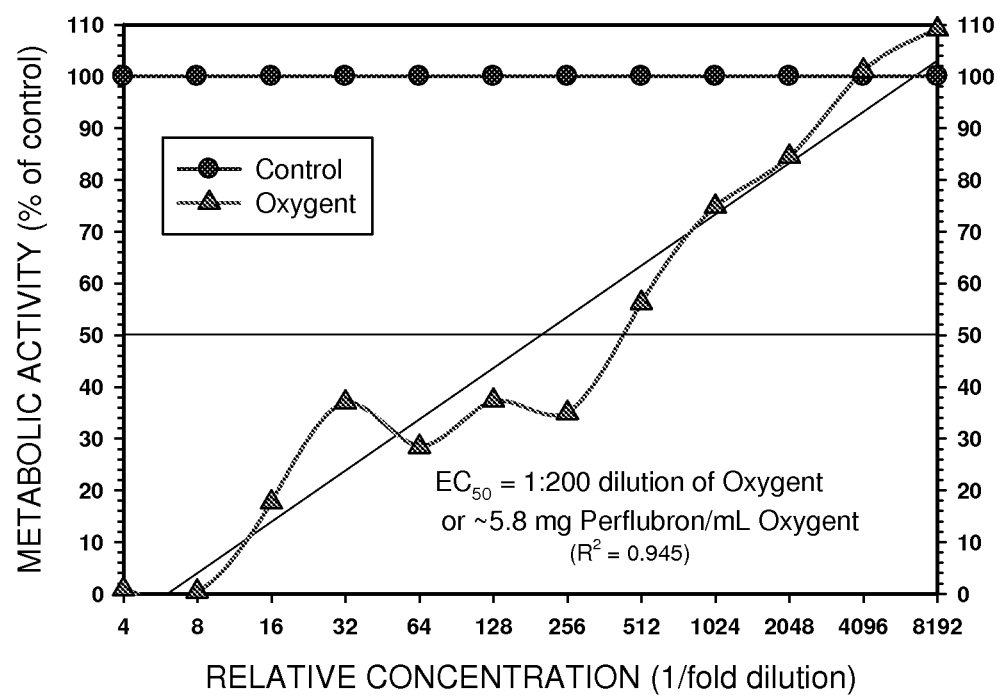
FIG. 2 graphically illustrates the effect of aerosol perfluorocarbon emulsion composition on the growth of SAOS-LM7 osteosarcoma cells.

In particular, breast cancer associated fibroblasts and osteosarcoma cells (SAOS-LM7) were cultured by methods known in the art. An aerosol of 60% perflubron/Egg Yolk Phospholipid emulsion (5.8 mg Perflubron/mL) using a nebulizer was administered to the cell populations (concentration of ~30%) for 1 minute. The metabolic activity was assayed using Almar Blue staining. The aerosolized fluorocarbon emulsions dramatically reduced the growth of breast cancer fibroblasts (FIG. 1) and osteosarcoma cells (FIG. 2).

Example 2

Treatment of Respiratory Distress

Figure 3:
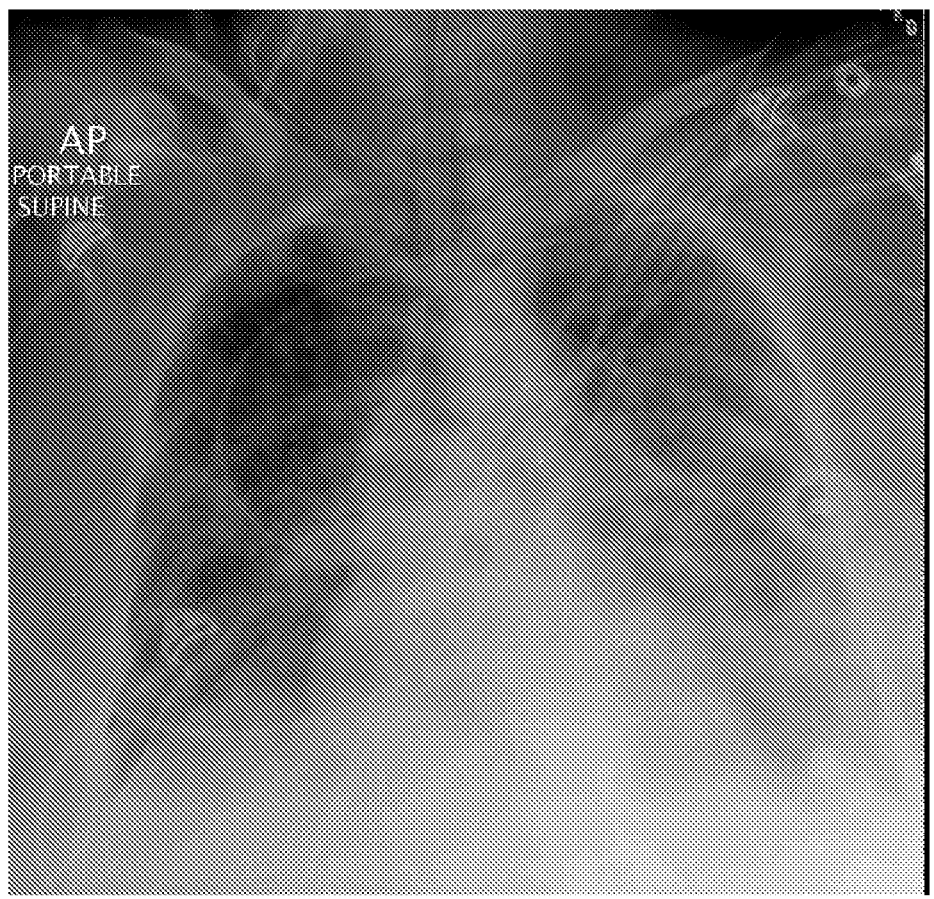
FIG. 3 shows a lung x-ray of a male infected with H1N1 influenza before treatment with aerosol perfluorocarbon emulsion composition.
Figure 4:
FIG. 4 shows a lung x-ray of a male infected with H1N1 influenza nine hours after treatment with aerosol perfluorocarbon emulsion composition.
Figure 5:
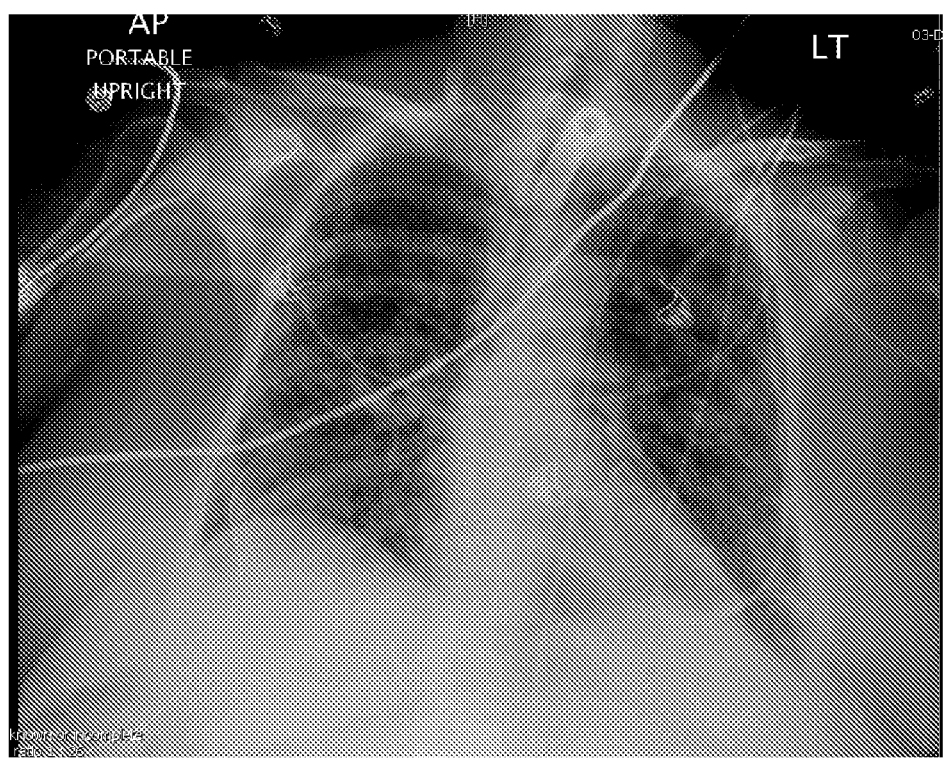
FIG. 5 shows a lung x-ray of a male infected with H1N1 influenza one week after treatment with aerosol perfluorocarbon emulsion composition.

A patient exhibiting acute respiratory distress syndrome (ARDS) was treated with an aerosolized fluorocarbon composition of the present invention. In particular, a 53 year old patient diagnosed with H1N1 associated ARDS was administered an aerosol of 60% perflubron/Egg Yolk Phospholipid emulsion using a nebulizer. The emulsion acted as a surfactant and oxygen therapeutic. The patient was administered two 50 mL doses and exhibited a dramatic improvement in radiographs and gas exchanged in 9 hours (compare FIG. 3 to FIG. 4). Improvement in oxygen saturation improved from 87% to 97% after a few hours of treatment. Airway mechanics and gas exchange continued to improve over a 1 week period (compare FIG. 3 to FIG. 5).

Example 3

Prophetic Treatment of Spinal Cord Injury

A subject harboring spinal cord injury will be treated with a 50% perflubron emulsion that has been oxygenated. The emulsion will be directly instilled above the injury site using a catheter tip. Fluid will be collected below the injury, re-oxygenated and applied above the injury again in a push-pull method. This process is continued for 1 to 48 hours and can be repeated if necessary.

Example 4

Prophetic Treatment of Macular Degeneration

A subject with macular degeneration will be treated with a 50% perflubron emulsion that has been oxygenated. The emulsion will be directly instilled onto the ocular surface. This process is continued for 1 to 48 hours and can be repeated if necessary.

Example 5

Prophetic Treatment of Cancer

Mice harboring EMT6 mammary tumors will be treated with an aerosolized 60% perflubron emulsion alone and in combination with gemcitabine. The perflubron emulsion will be administered at a dose of 3 mL of emulsion/kg body weight as an aerosol. The aerosol will be targeted to the tumor site using a catheter and administered 3 to 4 times over the course of a week. Mice will be housed in individual chambers of gassing boxes which will be flushed with the appropriate atmosphere, i.e. air or carbogen (95% $O_2$/5% $CO_2$) and provided such atmosphere for the duration of the treatment regimen. Tumor growth will be measured prior to treatment, 2 days after the first treatment, 1 day after the final treatment and 1 week following the final treatment.

Example 6

Prophetic Treatment of Cancer using Radiation Sensitivity

Mice harboring EMT6 mammary tumors will be treated with an aerosolized 65% perflubron emulsion. The perflubron emulsion will be administered at a dose of 3 mL of emulsion/kg body weight as an aerosol. The aerosol will be targeted to the tumor site using a catheter. Following administration of the aerosol, mice will be placed in individual chambers of Lucite gassing-irradiation boxes which will be flushed with the appropriate atmosphere, i.e. air or carbogen (95% $O_2$/5% $CO_2$) for 15 minutes before irradiation and throughout the irradiation process. Mice will be removed from the chamber and positioned for irradiation. Mice will breathe air or carbogen administered by a nose cone during positioning and irradiation. Mice will be irradiated with 250 kV x-rays at a dose rate of 6 Gy/min. Tumor growth will be measured prior to treatment, 2 days after treatment, and 1 week following the treatment.

Example 7

Fluorochemical Emulsion as a Delivery Vehicle

The ability of aerosolized fluorochemicals to deliver bioagents to a target and enhance their retention at that site makes them a novel therapeutic agent. To analyze the effectiveness of fluorochemicals as a delivery vehicle, different amounts of a bioactive agent were administered to a subject and the target site and agent retention were examined.

Figure 6:
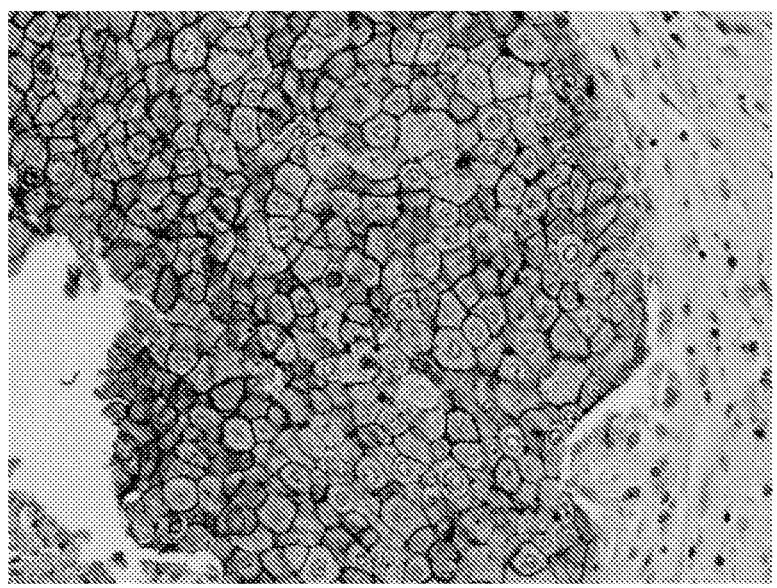
FIG. 6 shows the binding of a therapeutic agent (herceptin) on the target area (herceptin:$H_2O$ (at a dilution of 1:1500)) delivered in aerosol form.
Figure 7A:
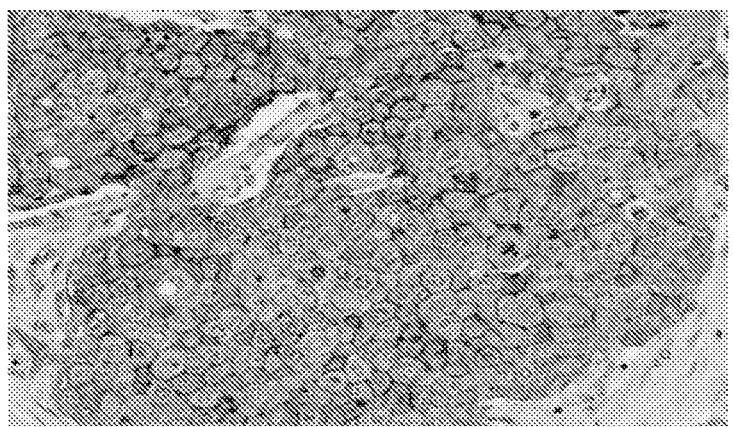
FIG. 7a shows immunostaining of tumor sample indicating the binding of a therapeutic agent (herceptin) on the target area (herceptin:perfluorochemical composition (at a dilution of 1:1500)) delivered in aerosol form.
Figure 7B:
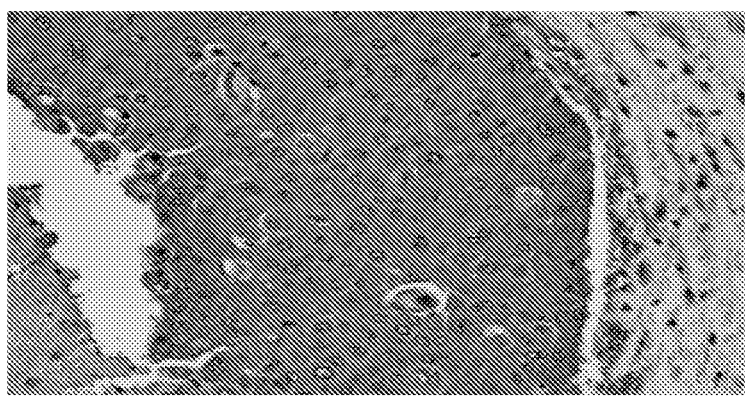
FIG. 7b shows immunostaining of tumor sample indicating the binding of a therapeutic agent (herceptin) on the target area (herceptin:perfluorochemical composition (at a dilution of 1:30,000)) delivered in aerosol form.

In particular, an aerosolized fluorocarbon emulsion containing the anti-cancer agent Herceptin was administered to a subject. The aerosol contained 60% perflubron/egg yolk phospholipid emulsion. Tumor biopsies were collected and analyzed using immunohistochemistry techniques and antibodies for detecting Herceptin. Herceptin was detected using a dilution of 1:1500 of antibody in tumors collected from subjects treated with Herceptin only (FIG. 6). Herceptin was detected at greater strength using a dilution of 1:1500 of detection antibody in tumors collected from subjects treated with an aerosolized fluorocarbon emulsion containing Herceptin (FIG. 7A). In these tumors, Herceptin could be detected using a dilution as much as 1:30,000 (FIG. 7B). These results indicate that the aerosolized fluorocarbon emulsion targeted the Herceptin to the target site and enhanced the retention of the Herceptin at the target site.

Example 8

Treatment of Metastatic Cancer

Figure 8A:
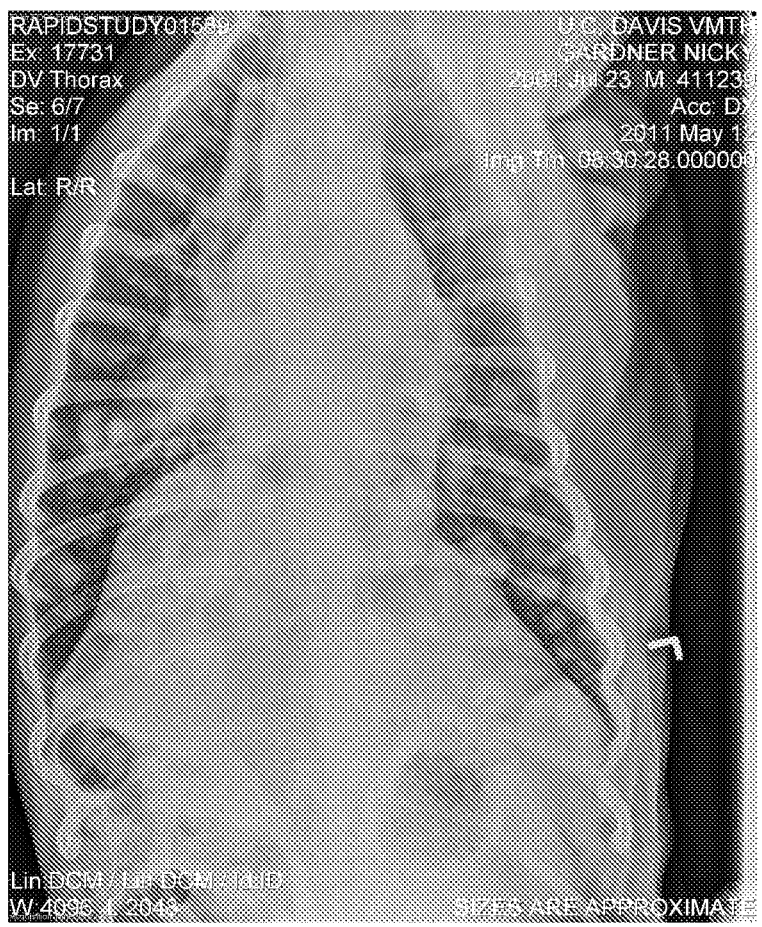
FIG. 8A shows an x-ray of the lungs of a dog with soft tissue sarcoma and lung metastasis. This figure shows the distal view of the dog's thorax.
Figure 8B:
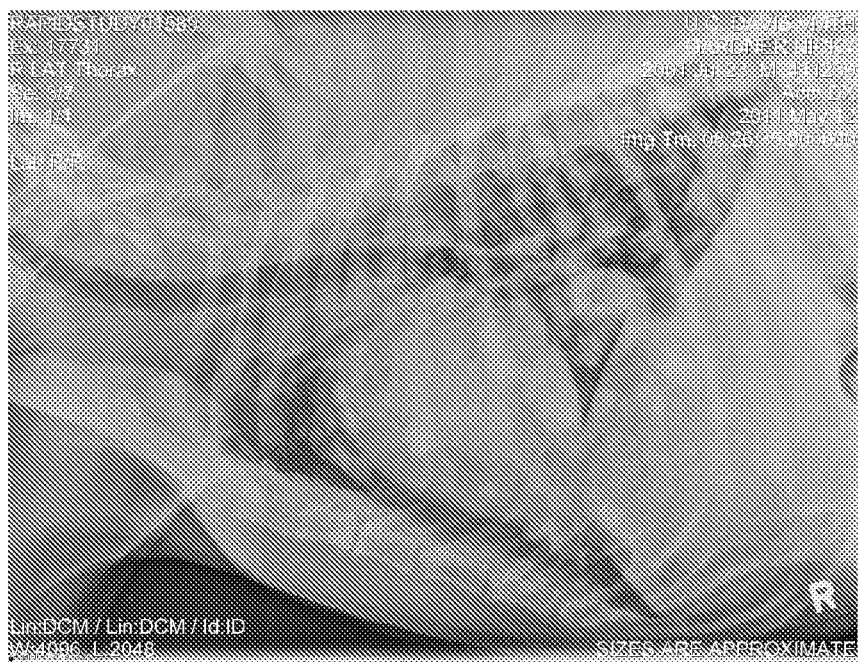
FIG. 8B shows an x-ray of the lungs of a dog with soft tissue sarcoma and lung metastasis. This figure shows the right lateral view of the dog's thorax.
Figure 9A:
FIG. 9A shows a Hemotoxylin and Eosin (H&E) stained microscopic section of a lung metastatic soft tissue sarcoma after treatment with aerosolized perflubron emulsion at 10× magnification.
Figure 9B:
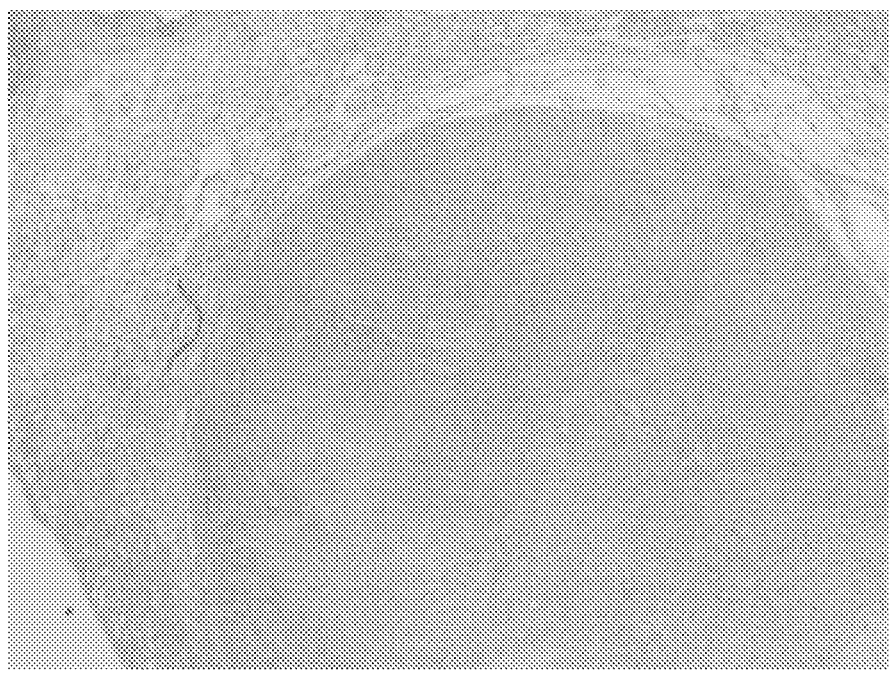
FIG. 9B shows a Hemotoxylin and Eosin (H&E) stained microscopic section of a lung metastatic soft tissue sarcoma after treatment with aerosolized perflubron emulsion at 5× magnification.

The effectiveness of treating a subject having metastatic cancer with an aerosol of 60% perflubron/egg yolk phospholipids containing anti-cancer agents was examined. A 9 year old Golden Retriever with soft tissue sarcoma and extensive lung metastasis was treated with 9 mg/ml twice weekly for 10 weeks by pulmonary aerosol administration (FIG. 7A & FIG. 7B). No necrosis was detected in the lung parenchyma (FIGS. 8A and 8B). Delivery of oxygen was enhanced in the lung parenchyma where the perflubron emulsion was targeted. In contrast, pleural lesions, which are on the outside of the lung and not targeted, had lower oxygen content. This lower oxygen content indicates that perflubron did not localize in pleural lesions and, thus, did not deliver the agent to these areas.

Further, the lung parenchyma lesions did not exhibit necrosis, but the pleural regions had gross necrosis. Notably, severe necrosis is always observed in both lung parenchyma and pleural metastasis when Gemcitabine is aerosolized alone. Thus, the results indicate that the aerosolized perflubron emulsion targets agents to target sites, enhances the retention of the agent at the target site and acts synergistically to enhance the activity of the agent.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

What is claimed is:

1. A method of inhibiting the activity of a fibroblast cell comprising contacting the fibroblast cell with a fluorochemical composition, wherein the fluorochemical composition comprises:
    a. a fluorochemical;
    b. a bioactive agent, wherein the bioactive agent is a tyrosine-kinase inhibitor based agent; and
    c. an emulsion agent, wherein the emulsion agent is selected from the group consisting of triperfluoroalkylcholate, perfluoroalkylcholestanol, perfluoroalkyloxymethylcholate, C3F7 O(CF2)3C(=O)NH(CH2)3N(O)(CH3)2 (XMO-10), fluorinated polyhydroxylated surfactants, polyoxyethylene-polyoxypropylene copolymers, and combinations thereof.

2. The method of claim 1, wherein the fluorochemical composition further includes an antibody.

3. The method of claim 2, wherein the tyrosine-kinase inhibitor is selected from the group consisting of afatinib, axitinib, bafetinib, bosutinib, cediranib, crizotinib, dasatinib, erlotinib hydrochloride, gefitinib, imatinib, lapatinib, lestaurtinib, neratinib, nilotinib, nintedanib, ponatinib, quizartinib, regorafenib, ruxolitinib, sunitinib tofacitinib, vandetanib, vatalanib, and combinations thereof.

4. The method of claim 2, wherein the antibody is selected from the group consisting of alemtuzumab, bevacizumab, cetuximab, gemtuzumab ozogamicin, ibritumomab tiuxetan, ofatumumab, panitumumab, rituximab, tositumomab, trastuzumab, trastuzumab DM1, and combinations thereof.

5. The method of claim 1, wherein the fluorochemical composition bioactive agent further comprises an imaging agent.

6. The method of claim 1, wherein the fluorochemical is selected from the group consisting of bis(F-alkyl) ethanes, cyclic fluorocarbons, perfluorinated amines, brominated perfluorocarbons, perfluorooctyl chloride, perfluorooctyl hydride, perfluoroalkylated ethers, perfluoroalkylated polyethers, fluorocarbon-hydrocarbon compounds, and combinations thereof.

7. A method of inhibiting the activity of a fibroblast cell comprising contacting the fibroblast cell with a fluorochemical composition, wherein the fluorochemical composition is an aerosol and comprises (a) a perfluorocarbon; (b) tyrosine-kinase inhibitor; and (c) an emulsifier comprising 1% to 6% (w/v) phospholipid.

8. The method of claim 7, wherein the phospholipid is selected from the group consisting of lecithin, egg yolk phospholipids, and combinations thereof.

9. The method of claim 7, wherein the nonionic surfactant is selected from the group consisting of polyoxyethylene-polyoxypropylene copolymers, and combinations thereof.

10. A method of treating cancer in a subject comprising administering a fluorochemical composition to the subject in need thereof, wherein the fluorochemical composition comprises a fluorochemical, a bioactive agent that affects tyrosine-kinase activity, and an emulsion agent.

11. The method of claim 10, wherein the fluorochemical composition is applied directly to the location of the cancer in the subject as an aerosol or as a liquid.

12. An aerosolized fluorochemical composition comprising a fluorochemical, a bioactive agent that affects tyrosine-kinase activity; and 1% to 6% (w/v) of an emulsion agent, wherein the emulsion agent is selected from the group consisting of triperfluoroalkylcholate, perfluoroalkylcholestanol, perfluoroalkyloxymethylcholate, C3F7 O(CF2)3C(=O)NH(CH2)3N(O)(CH3)2 (XMO-10), fluorinated polyhydroxylated surfactants, polyoxyethylene-polyoxypropylene copolymers, a phospholipid and combinations thereof.

13. The aerosolized fluorochemical composition of claim 12, wherein the bioactive agent that affects tyrosine-kinase activity is an antibody, a tyrosine-kinase inhibitor, or both.

14. The aerosolized fluorochemical composition of claim 12, further comprising an imaging agent.

15. The aerosolized fluorochemical composition of claim 13, wherein the fluorochemical is 1-bromo-heptadecafluorooctane.

16. The aerosolized fluorochemical composition of claim 13, wherein the emulsion agent is an egg yolk phospholipid.

* * * * *